US009692036B2

(12) United States Patent
Bennett et al.

(10) Patent No.: US 9,692,036 B2
(45) Date of Patent: Jun. 27, 2017

(54) DESTRUCTIVE BATTERY CLOSURE

(71) Applicant: GYRUS ACMI, INC., Southborough, MA (US)

(72) Inventors: Michael J. Bennett, Bartlett, TN (US); Phillip A. Ryan, Memphis, TN (US); Paul E. Yarbrough, Stanton, TX (US); Richard Roth, Brookline, NH (US)

(73) Assignee: GYRUS ACMI, INC., Southborough, MA (US)

( * ) Notice: Subject to any disclaimer, the term of this patent is extended or adjusted under 35 U.S.C. 154(b) by 92 days.

(21) Appl. No.: 14/703,158

(22) Filed: May 4, 2015

(65) Prior Publication Data
US 2015/0236332 A1  Aug. 20, 2015

Related U.S. Application Data

(63) Continuation-in-part of application No. 14/012,190, filed on Aug. 28, 2013, now Pat. No. 9,065,107.
(Continued)

(51) Int. Cl.
*H01M 2/34* (2006.01)
*H01M 2/20* (2006.01)
*H01M 2/10* (2006.01)

(52) U.S. Cl.
CPC ........... *H01M 2/34* (2013.01); *H01M 2/1022* (2013.01); *H01M 2/204* (2013.01); *H01M 2220/30* (2013.01)

(58) Field of Classification Search
None
See application file for complete search history.

(56) References Cited

U.S. PATENT DOCUMENTS 5,112,299 A    5/1992  Pascaloff
5,149,603 A *  9/1992  Fleming ............. H01M 2/1055
                                                    429/100
(Continued)

FOREIGN PATENT DOCUMENTS

CN         2648610      10/2004
CN       102113150       6/2011
(Continued)

OTHER PUBLICATIONS

Federal Register, vol. 76, No. 27 issued Feb. 9, 2011 which details Supplementary Examination Guidelines for Determining Compliance with 35 U.S.C. 112 and for Treatment of Related Issues in Patent Applications.*
(Continued)

*Primary Examiner* — Ula C Ruddock
*Assistant Examiner* — Amanda Barrow
(74) *Attorney, Agent, or Firm* — The Dobrusin Law Firm, P.C.

(57) ABSTRACT

An article including: a battery support containing battery lead wires attached to terminals; an opposing battery support attached to the battery support to create a battery closure; one or more batteries having battery contacts in the opposing battery support; and one or more activation tabs; wherein the terminals are attached to spring-loaded members; wherein the one or more activation tabs are spaced between the terminals and the battery contacts; wherein the spring-loaded members provide a biasing force that biases the terminals against the activation tabs keeping the one or more activation tabs in place in either a first position or a second position of the opposing battery support; wherein the opposing battery support is securely connected to the battery support in both the first position and the second position; and
(Continued)

wherein the biasing force is greater in the second position than in the first position.

20 Claims, 12 Drawing Sheets

Related U.S. Application Data

(60) Provisional application No. 61/694,522, filed on Aug. 29, 2012.

(56) References Cited

U.S. PATENT DOCUMENTS

| | | | |
|---|---|---|---|
| 5,265,275 A * | 11/1993 | Goldenberg | H01M 2/1055 |
| | | | 361/814 |
| 5,537,022 A * | 7/1996 | Huang | H02J 7/0042 |
| | | | 320/107 |
| 5,814,044 A | 9/1998 | Hooven | |
| 7,879,032 B1 | 2/2011 | Garito et al. | |
| 2003/0149424 A1 | 8/2003 | Barlev et al. | |
| 2004/0018420 A1 * | 1/2004 | Nakajima | H01M 2/1022 |
| | | | 429/97 |
| 2004/0092992 A1 | 5/2004 | Adams et al. | |
| 2007/0093868 A1 | 4/2007 | Fugo | |
| 2008/0063926 A1 * | 3/2008 | Huang | H01M 2/105 |
| | | | 429/96 |
| 2008/0065001 A1 | 3/2008 | DiNucci et al. | |
| 2009/0057369 A1 | 3/2009 | Smith et al. | |
| 2010/0198009 A1 | 8/2010 | Farr et al. | |
| 2011/0064978 A1 * | 3/2011 | McGahan | A61B 17/7091 |
| | | | 429/61 |
| 2011/0189514 A1 | 8/2011 | Lee et al. | |
| 2012/0059231 A1 | 3/2012 | Frey et al. | |
| 2012/0115007 A1 * | 5/2012 | Felder | A61B 17/00234 |
| | | | 429/121 |
| 2012/0276428 A1 * | 11/2012 | Pendry | H01M 2/1055 |
| | | | 429/90 |
| 2013/0009606 A1 * | 1/2013 | Smith | A61B 50/20 |
| | | | 320/137 |
| 2013/0164587 A1 * | 6/2013 | Smith | H01M 2/1066 |
| | | | 429/97 |
| 2014/0175149 A1 * | 6/2014 | Smith | A61B 90/90 |
| | | | 227/175.2 |

FOREIGN PATENT DOCUMENTS

| | | | | |
|---|---|---|---|---|
| DE | 2136749 A1 | 2/1973 | | |
| EP | 0494505 | * 7/1992 | | H01M 2/10 |
| JP | 2010-540192 | 12/2010 | | |
| JP | 2013-543390 | 12/2013 | | |
| WO | 99/03186 A1 | 1/1999 | | |
| WO | 2010/075438 A1 | 7/2010 | | |
| WO | 2011/141752 A2 | 11/2011 | | |
| WO | 2013/057043 A1 | 4/2013 | | |

OTHER PUBLICATIONS

PCT Search Report and Written Opinion dated Nov. 27, 2013; Application No. PCT/US2013/057058.
PCT Search Report and Written Opinion dated Nov. 26, 2013; Application No. PCT/US2013/057043.
International Preliminary Report on Patentability dated Mar. 12, 2015, Application No. PCT/US2013/057043.
International Preliminary Report on Patentability dated Mar. 12, 2015, Application No. PCT/US2013/057058.
Japanese Office Action for Application No. 2015-524513 dated Jul. 8, 2015.
European Patent Office Action for Application No. 13760187.8 dated Oct. 5, 2015.
State Intellectual Property Office of China Office Action for Application No. 201380027915.5 dated Mar. 17, 2016.

* cited by examiner

DESTRUCTIVE BATTERY CLOSURE

CLAIM OF PRIORITY

This application is a continuation-in-part of Ser. No. 14/012,190 filed on Aug. 28, 2013, and claims priority therefrom incorporated herein by reference.

FIELD

The present invention relates generally to power sources for devices, and more particularly to a battery closure supplying energy to a motor of a disposable device.

BACKGROUND

Different versions of battery closures supplying energy to disposable devices are known, for example U.S. Pat. Nos. 5,112,299; 5,814,044; 7,879,032; or U.S. Patent Application No. 2004/0092992, all of which are expressly incorporated by reference in their entirety herein for all purposes. When producing a disposable device, a manufacturer may want to ensure that the disposable device will not be reused. This is especially imperative concerning medical disposable devices where enforcing single use contributes to patient safety. Disposable devices limiting user's utility of the device by a variety of mechanisms are known in the art. The problem is that such devices do not prevent insertion of a new battery or recharging of the existing batteries, thus allowing reuse of the disposable device which should be disposed of after a single use.

Additionally, a user of a disposable device may want to dispose of a disposable device without having to discard it with the batteries powering the device; therefore contributing to environmental safety. A user of such a disposable medical device may be inclined to do so especially when the disposable device is a medical device which may have to be disposed of as a medical or bio hazardous waste while the batteries may be recycled. The problem is that many of the known disposable devices do not provide for disabling the battery circuit and do not allow a user to remove the batteries; therefore the disposable medical instruments have to be discarded with the batteries included which poses environmental issues and prevents use of the instruments in facilities requiring special disposal of batteries.

Therefore, there is need for a battery closure supplying energy to a motor of a disposable device which would enforce a single use of the disposable device by preventing supply of energy to the motor after the disposable device has been used and allowing removal of the batteries from the battery closure in such a way that the disposable device can be disposed of separately from the batteries.

SUMMARY

An article comprising: (a) a battery support containing battery lead wires, (b) an opposing battery support attached to the battery support to create a battery closure, and (c) one or more batteries; wherein the batteries are secured to the opposing battery support, the batteries supply energy to a device, and removing the opposing battery support from the battery closure disables transmission of electricity from the batteries via the battery lead wires to the device.

An article comprising: (a) a battery support containing battery lead wires; (b) an opposing battery support to be attached to the battery support to create a battery closure; (c) one or more batteries having one or more battery contacts in the opposing battery support; and (d) one or more activation tabs; wherein the one or more terminals are attached to the one or more spring-loaded members; wherein the one or more activation tabs are spaced between the one or more terminals and the one or more battery contacts; wherein the one or more spring-loaded members provide a biasing force that biases the one or more terminals against the one or more activation tabs in place in either a first position or a second position; wherein the opposing battery support is securely connected to the battery support in both the first position and the second position; and wherein the biasing force is greater in the second position than in the first position.

Another embodiment includes: an article comprising: (a) a battery support containing battery lead wires attached to one or more terminals, (b) an opposing battery support to be attached to the battery support to create a battery closure, wherein the opposing support has a first position and a second position and the distance between the terminals and the battery contacts is greater in the first position than in the second position, (c) one or more batteries having one or more battery contacts in the opposing battery support, and (d) one or more activation tabs; wherein the terminals are attached to one or more spring-loaded members, the one or more activation tabs are spaced between the terminals and the battery contacts, and the spring-loaded members hold the one or more activation tabs between the one or more terminals and the one or more battery contacts, keeping the activation tabs in place in both the first position and the second position.

Another embodiment includes: a disposable medical device comprising: (a) a housing, (b) a powered element within the housing, (c) a battery support containing battery lead wires, (d) an opposing battery support attached to the battery support to create a battery closure, (e) one or more batteries; (f) a battery bulkhead, (g) a first battery bulkhead joining member, and (h) a second battery bulkhead joining member; wherein the first battery bulkhead joining member attaches the battery bulkhead to the battery support, and the second battery bulkhead joining member attaches the battery bulkhead to the opposing battery support; the battery support allows mechanical release of the opposing battery support from the battery closure once coupled in either a first or a second position; the battery bulkhead stays engaged to the battery support by the first battery bulkhead joining member when the opposing battery support is in the first position; the battery bulkhead is retained in the second battery bulkhead joining member and released from the first battery bulkhead joining member when the opposing battery support is in the second position; a first section of the battery lead wires is attached to the battery support, a second section of the battery lead wires is attached to the bulkhead, and an intermediate section of the battery lead wires between the first section and the second section contains a solder joint that ruptures when a user removes the opposing battery support from the battery closure which disables and severs the battery lead wires.

The disclosure further comprises a method of using the article, including: (i) preventing supplying energy to a device by: (a) assembling a battery closure by connecting a battery support to an opposing battery support, wherein the battery support contains battery lead wires attached to one or more terminals and one or more batteries are secured to the opposing battery support; (b) preventing engaging the one or more batteries by one or more spring-loaded members holding the one or more terminals against one or more activation tabs when the opposing battery support is in either a first position or a second position; and (ii) supplying energy to the device by: (a) removing the one or more activation tabs; and (b) driving the one or more terminals by the one or more spring-loaded members into contact with the one or more battery contacts so as to engage the one or more batteries and the one or more battery lead wires to establish contact between the one or more battery contacts and the one or more battery lead wires.

Preferably, a user can dispose of the opposing battery support with the one or more batteries separately from the device. Preferably, the battery closure does not allow electrical reconnection after the opposing battery closure is removed. Preferably, the article further comprises a device which is a disposable medical device. Preferably, a first section of the battery lead wires is attached to the battery support. Preferably, the article further comprises: a battery bulkhead, a first battery bulkhead joining member, and a second battery bulkhead joining member; wherein the first battery bulkhead joining member attaches the battery bulkhead to the battery support, and wherein the second battery bulkhead joining member attaches the battery bulkhead to the opposing battery support.

The present teachings provide a battery closure and a method of using a battery closure supplying energy to a device which does not allow for replacement of batteries within the battery closure; therefore enforcing a single use of the device and in case of medical disposable devices, increasing patient safety and validation of sterilization. This advantage of the present invention is accomplished by inclusion of a mechanism which disables battery lead wires when a user attempts to replace the batteries. The additional advantage is that the mechanism disabling the battery lead wires is utilized when a user wants to discard the batteries separately from the device as the mechanism disabling battery lead wires can sever the lead wires and enables the user to remove a battery cover containing the severed battery lead wires and securely attached batteries; therefore, the batteries can be disposed of separately from the device. The advantage of this feature of the present invention lies in an environmentally friendly disposal and recycling of the batteries separately from biomedical waste which may be environmentally and economically advantageous. An additional advantage of the present invention is that the invention's mechanism preventing reuse of the device may be a mechanically simple, low-cost mechanism which may be used for battery closures incorporated into the device as well as battery closures externally attached to the device.

DETAILED DESCRIPTION

Figure 1:
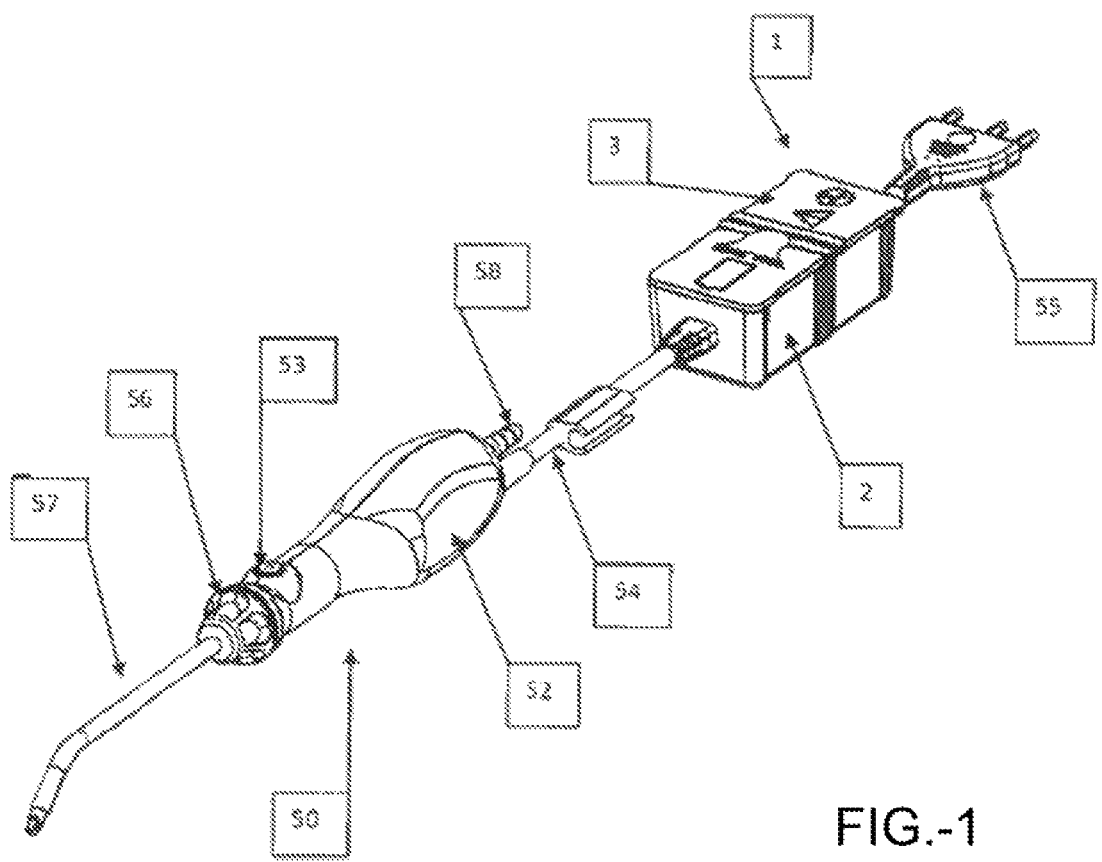
FIG. 1 illustrates an article including a battery closure of the teachings herein.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings provide a destructive battery closure supplying energy to a device such as a disposable medical device, and other devices. A disposable medical device may be for example an electrosurgical debrider such as a tonsil and adenoid debrider. Preferably, the device has a hand-held portion wherein power is provided to the functioning portion of the device by one or more batteries. More preferably, the device is a light-weight, portable hand-held device. The device may comprise a housing, a handle, a powered element, a motor, a light-emitting diode (LED), a circuit, a light, a motor within the housing powered by the one or more batteries in the battery closure, motor lead wires, a light-emitting diode activation light, an external cable leading from the device to a functional system such as a console, a suction port, a hose providing suction, a suction tip, a rotating nose cone, a rotating inner blade placed within an external tube, a shaver blade, one or more electrodes, and the like.

The battery closure holds, secures, and protects batteries which supply electrical energy to a powered element, such as a motor, an LED, a circuit, a light, and the like, in the housing of the device. The battery closure may have any size, shape, configuration, or a combination thereof. The battery closure may be made of any material with a low electrical conductivity commonly utilized in battery closures for devices. Preferably, the material is also lightweight. More preferably, the material withstands a variety of environmental conditions to which devices used in the invention may be exposed to, for example caustic fluids, radiation, steam, varying temperatures, vacuum, and/or physical abuse. The preferred materials are acrylonitrile butadiene styrene (ABS), polycarbonate (PC), or a blend of ABS and PC, polyolefins, polystyrene, and blends thereof. The battery closure may further contain an elastic member which may be applied over the battery closure to further protect it from external exposure. The battery closure may also contain a crude splash resistant sealing to prevent the battery closure against fluids. The battery closure may be located outside of the housing such as be attached and/or wired to an external cable or be located inside of the housing. The battery closure may be attached and/or wired to an external cable leading from the housing to the battery closure. Preferably, if the device is a medical device, the battery closure is attached to the external cable at a certain distance, away from the medical device, to keep the sterile environment around a patient. The battery closure comprises a battery support, an opposing battery support, one or more batteries, battery lead wires, and the like. Various parts of the battery closure, such as the battery support, the opposing battery support, the opposing battery support's handle, or the like may contain signage such as "ON," "OFF," arrows, or the like to offer a user visual affirmation of the position the battery closure is in. The battery closure can be disassembled by separating the battery support and the opposing battery support. When the battery lead wires are disabled and/or the battery closure is separated, the battery closure no longer functions to transmit electricity from the batteries via the battery leads wires to the device and does not allow for electrical reconnection after the opposing battery closure is removed.

The battery support protects and supports the batteries and accommodates a battery bulkhead with battery lead wires. The battery support may have any size, shape, configuration, or a combination thereof so that the battery support can form the battery closure and can accommodate the opposing battery support with one or more batteries and house battery lead wires. The battery support may be made of any material with a low electrical conductivity commonly utilized in battery supports. Preferably, the material is also lightweight. More preferably, the material withstands a variety of environmental conditions to which devices used in the invention may be exposed to, for example caustic fluids, radiation, steam, varying temperatures, vacuum, and/or physical abuse. The battery support may be connected and/or wired to an external cable leading from the housing to the battery support. The battery support may be connected and/or wired to an additional cable leading to a console. Preferably, the battery support has a mechanism for ensuring a secure fit of the opposing battery support into the battery support so that once a user assembles the battery closure by connecting the battery support to the opposing battery support, the battery closure does not disassemble and release the batteries. The mechanism can comprise at least one member which snaps, slides, hooks into, latches onto, attaches, or the like into a corresponding member on the opposing battery support. The preferred mechanism for ensuring a secure fit of the opposing battery support into the battery support is a snap and slide. The battery support may further comprise members corresponding to the first battery bulkhead joining member of the battery bulkhead. The members may have any size, shape, configuration, or a combination thereof so that they accommodate the first battery bulkhead joining member, ensuring that the battery bulkhead couples to the battery support. Preferably, the members are sockets and/or slots. The battery support may further contain a mechanism for disabling the battery lead wires. Once a user disables the battery lead wires, the electrical energy is no longer capable of being transmitted between the batteries and the device. More preferably, the battery support and/or the opposing battery support may contain a mechanism for severing the battery lead wires from the battery support, such as a blade within a bulkhead capable of cutting the battery lead wires when a user removes the opposing battery support from the battery closure. Alternatively, the mechanism may comprise a member engaging the opposing battery support's corresponding member which will sever the battery lead wires in the battery support; preferably comprising of at least one arm with at least one pin in the opposing battery support and at least one track in at least one side wall of the battery support engaging the at least one pin wherein the battery lead wires are disabled by being severed and the battery bulkhead removed from the battery support by the at least one arm.

The battery bulkhead holds battery lead wires and provides contact of the battery contacts with the battery lead wires. The battery bulkhead may be any structure performing this function. The battery bulkhead may have any size, shape, configuration, or a combination thereof so that the battery bulkhead fits within the battery closure and accommodates the battery lead wires. The battery bulkhead is made of any material with a low electrical conductivity which is typically utilized in battery bulkheads, such as plastic. Preferably, the material is also lightweight. The battery bulkhead may be attached to the battery support and alternatively to the opposing battery support with the battery bulkhead joining members. Preferably, a first battery bulkhead joining member attaches the battery bulkhead to the battery support and a second battery bulkhead joining member attaches the battery bulkhead to the opposing battery support. The battery bulkhead may contain battery bulkhead joining members. The battery bulkhead joining members can be any structure serving this function. The battery bulkhead joining members may have any size, shape, configuration, or a combination thereof. Preferably, the first battery bulkhead joining member is a set of posts on the bottom of the bulkhead fitting into corresponding members, such as sockets, in the battery support, and/or a pair of lateral ears on the sides of the bulkhead fitting into corresponding members, such as slots, on the inner sides of the battery support. The battery bulkhead stays engaged to the battery support by the first battery bulkhead joining member when the opposing battery support is in the first position, and the battery bulkhead is retained in contact with the second battery bulkhead joining member and released from the contact with the first battery bulkhead joining member when the opposing battery support is in the second position. The battery bulkhead may have an undercut which serves to remove the battery bulkhead from the battery support when a user disassembles the battery closure. The battery bulkhead may further contain a power regulator designed to maintain a constant voltage level of output. The power regulator may be any size, shape, configuration, or a combination thereof. The power regulator may be located on the bulkhead facing the front edge of the battery support. The battery bulkhead may contain a blade for disabling and severing battery leads. The battery bulkhead is located in the battery support. Preferably, the battery bulkhead is located in the front portion of the battery support between the space into which the opposing battery support's battery compartment is inserted and the front edge of the battery support. The battery bulkhead is attached to the battery support when the opposing battery support is in the first position. Preferably, the battery bulkhead holding the battery lead wires is attached to the battery support with at least one battery bulkhead joining member when the opposing battery support is in the first position. The battery bulkhead is not attached to the battery support and is coupled to the opposing battery support with at least one second battery bulkhead joining member when the opposing battery support is in the second position.

The battery lead wires provide transmission of electrical energy between the batteries and the device. The battery lead wires may have any size, shape, configuration, or a combination thereof. The battery lead wires are made of any material which is typically utilized in battery lead wires. Preferably, the battery lead wires are made of a material capable of transmitting electric energy from the battery contacts to the device. Preferably, the battery lead wires are flexible, corrosion resistant, and capable of wet applications. The battery lead wires may have a plurality of sections. Preferably, the battery lead wires have a first section, a second section, and an intermediate section. More preferably, the first section of the battery lead wires is attached to the battery support; the second section of the battery lead wires is attached to the bulkhead; and the intermediate section of the battery lead wires is located between the first section and the second section. Preferably, the second section of the battery lead wires is physically captured in the battery bulkhead. Preferably, the battery lead wires are attached to the battery support, and/or the battery bulkhead in such a way that when a user removes the opposing battery support from the battery closure, the battery lead wires are disabled and/or severed. In one embodiment, the intermediate section contains a weakened section, such as a solder joint, which ruptures when a user removes the opposing battery support from the battery closure which disables and/or severs the battery lead wires. The battery lead wires may be in direct contact with the battery contacts. The battery leads may be in direct contact with an activation tab which prevents transmission of electricity from the battery contacts to the device via the battery lead wires. The battery lead wires may have one or more terminals which put the battery lead wires in contact with the activation tab and/or battery contacts. The battery lead wires may further be attached to one or more spring-loaded members biasing the battery leads with or without the terminals against the battery contacts and/or the activation tab.

The one or more terminals put the battery lead wires in contact with the battery contacts. The terminals may have any size, shape, configuration, or a combination thereof. The battery terminals may be made of any conductive material typically utilized in terminals. The terminals are attached to the battery lead wires. Preferably, the terminals are soldered to the battery lead wires. The terminals may be further attached to one or more spring-loaded members biasing the terminals against the activation tab and/or the battery contacts. In one embodiment, the terminals are attached to one or more spring-loaded members, and the distance between the terminals and the battery contacts is different when the opposing battery support is in the first position than in the second position, such as the distance is greater when the opposing battery support is in the first position. The terminals may be in contact with the one or more activation tabs before the activation tabs are removed by a user. After a user removes the activation tab, the terminals are in contact with the battery contacts and enable transmission of electrical energy from the batteries to the battery lead wires.

The one or more spring-loaded members hold the terminals against the activation tab preventing electrical contact between the battery contacts and the battery lead wires and assuring that the activation tab keeps its position before a user removes the activation tab. Additionally, the spring-loaded members drive the terminals to the battery contacts once the activation tab is removed. In one embodiment, the spring-loaded members may hold the one or more activation tabs between the one or more terminals and the one or more battery contacts, keeping the activation tabs in place when the opposing battery support is in the first or second position. The spring-loaded members may be any structure performing this function. The spring-loaded members may have any size, shape, configuration, or a combination thereof. The spring-loaded members may be compression springs, such as linear compression springs, extension springs, leaf springs, or the like. The spring-loaded members may be made of any conductive or non-conductive material capable of biasing typically utilized in spring-loaded members. The one or more spring-loaded members may provide a biasing force. The biasing force may bias the one or more terminals against one or more activation tabs; thereby keeping the one or more activation tabs in a first position, a second position, or both a first position and second position. The biasing force may increase through compression, such as with a linear compression spring. The biasing force may increase without increasing compression, such as with an extension spring or leaf spring. The spring-loaded members may be attached to the terminals, the battery lead wires, the bulkhead, the battery support, or a combination thereof. In one embodiment, the conductive or non-conductive spring-loaded members are placed between the battery bulkhead and the terminals or the battery bulkhead and the battery contacts. In another embodiment, the conductive or non-conductive spring-loaded members are placed between a surface of the battery support, such as an interior wall of the battery support, and the one or more terminals. The spring-loaded members may have a first end and a second end. The first end may be connected to the one or more terminals. The second end may be connected to an anchoring surface. The anchoring surface may be the battery bulkhead or a surface of the battery support. For example, the anchoring surface may the surface of the battery bulkhead facing toward the one or more battery contacts. For example, the anchoring surface may be an interior wall of the battery support, such as the interior wall facing the one or more battery contacts. The distance between the one or more terminals and the anchoring surface may be different in the second position than in the first position. For example, the distance between the one or more terminals and the anchoring surface may be greater in the first position than in the second position. For example, the distance between the one or more terminals and an interior wall of the battery support may be greater in the first position than in the second position. For example, the distance between the one or more terminals and the battery bulkhead may be greater in the first position than in the second position. In one embodiment, the terminals are attached to one or more spring-loaded members, and the biasing force is different when the opposing battery support is in the first position than in the second position. For example, the biasing force may be greater in the second position than in the first position.

The opposing battery support protects and houses one or more batteries and insulates the battery closure from the environment. The opposing battery support may have any size, shape, configuration, or a combination thereof so that a battery closure can be securely enclosed when a user sets the opposing battery support on the battery support. The opposing battery support's top may be any size, shape, configuration, or a combination thereof such as the top may be flat or contain attachments such as a handle. The opposing battery support may be made of any material with high dielectric constant which is typically utilized in the opposing battery supports such as plastic. Preferably, the material is also lightweight. More preferably, the material withstands a variety of environmental conditions to which devices used in the invention may be exposed to, for instance caustic fluids, radiation, steam, varying temperatures, vacuum, and/or physical abuse. Preferably, the opposing battery support has a mechanism for ensuring a secure fit of the opposing battery support into the battery support so that once a user assembles the battery closure by connecting the battery support to the opposing battery support, the battery closure does not disassemble and release the batteries. The mechanism can comprise at least one member which snaps, slides, hooks into, latches onto, attaches, or the like into a corresponding member on the battery support such as friction fits on chamfered bosses. The opposing battery support may be set on the battery support in a plurality of different positions. Preferably, the opposing battery support may be in three different positions once set on the battery support: a resting position, a first position, and the second position. To place the opposing battery support in the resting position, a user places the opposing battery support on top of the battery support without connecting the opposing battery support into the battery support. To place the opposing support in the first position, user securely connects the opposing battery support to the battery support. Preferably, a user activates the mechanism for ensuring a secure fit by snapping, sliding, hooking, latching, attaching, or the like the opposing battery support into the battery support in the first position. To place the opposing support in the second position, a user establishes a contact between the battery contacts and the battery lead wires or the terminals of the battery lead wires. Preferably, a user can establish the contact by sliding the opposing battery support forward and/or removing the activation tab, or sliding the opposing battery support forward to clear a gap between the battery terminals and the battery contacts. The opposing battery support may be moved from the first position to the second position by moving the opposing battery support along a linear axis of the one or more spring-loaded members. By sliding the opposing battery support towards the one or more spring-loaded members, the biasing force may increase. For example, if the spring-loaded members are linear compression springs, the biasing force is increased as the opposing battery support compresses the linear compression springs. The opposing battery support may further contain a handle on top of the opposing battery support for carrying the opposing battery support and/or battery closure once assembled, for ease of moving the opposing battery support from the first position to the second position, and for ease of disabling the battery lead wires and disassembling the battery closure by removing the opposing battery support. Preferably, a user may pull the opposing battery support by pulling the handle upward. More preferably, a user may pull the opposing battery support when the battery support is in either position as the battery support allows mechanical release of the opposing battery support from the battery closure once coupled in either the first or the second position. The handle may have any size, shape, configuration, or a combination thereof. The handle may be made of any material with low electrical conductivity which is typically utilized in handles for battery closures such as plastic. Preferably, the material is also lightweight. The opposing battery support may further contain a compartment for the one or more batteries which are either inserted before the device is shipped to the user in the initial or engaged positions or a user may secure the batteries to the opposing battery support. The secure placement of the batteries prevents replacement of the one or more batteries within the battery closure. The preferred way to secure the batteries is a snap fit of the batteries into the battery compartment of the opposing battery support. The opposing battery support may further contain an activation tab. A user can establish a contact between the battery lead wires and battery contacts by removing the activation tab. Alternatively, the activation tab may be absent and a contact between the battery lead wires and the battery contacts may be established by setting the opposing battery support into the second position. Preferably, a user is not able to slide the opposing battery support rearward once the opposing battery support is in the second position, thus preventing replacement of the one or more batteries within the opposing battery support and enforcing a single use of the device. Once the battery closure is assembled, and preferably, once a user utilized the device, a user may disable the battery lead wires. Preferably, a user disables the battery lead wires by removing the opposing battery support with the coupled battery bulkhead. The battery bulkhead is coupled to the opposing battery support after a user moves the opposing battery support in the second position. Preferably, the opposing battery support contains a second battery joining member which attaches the battery bulkhead to the opposing battery support. The second battery bulkhead joining member may be any structure serving this function. The second battery bulkhead joining member may be any size, shape, configuration, or a combination thereof so that the second battery bulkhead joining member overpowers the first battery bulkhead joining member attaching the battery bulkhead to the battery support. Preferably, the second battery bulkhead joining member is at least one arm.

More preferably, a user may sever the battery lead wires by removing the opposing battery support with the coupled battery bulkhead. For example, a user may remove the opposing battery support by lifting, pulling, forcing, cutting, unsnapping, unhooking, disattaching, sliding, or the like, the opposing battery support from the battery closure. More preferably, a user removes the opposing battery support by prying the opposing battery support's front edge, extending over the front edge of the battery support, upward to disable and/or sever the battery lead wires. The opposing battery support may further contain a lock which attaches to the rear side of the opposing battery support in the second position which allows a user to pull the opposing battery support only from the front side of the battery closure.

The one or more batteries provide electrical energy to the device, specifically to the motor of the device. The one or more batteries may be any size, shape, configuration, or a combination thereof so that they securely fit within the opposing battery support's battery compartment and supply sufficient amount of energy to the device. The one or more batteries may be any shape such as round, not round, flat or square. The one or more batteries may be made of any material typically utilized in batteries of devices such as various metals such as zinc-carbon, zinc-chloride, zinc-manganese, nickel oxyhydroxide, nickel-cadmium, nickel-zinc, lithium, or the like, carbon, or polymers. The one or more batteries may be any type typically utilized in devices such as triple-A batteries, double-A batteries, 9-Volt batteries, 4.5-Volt batteries, D batteries, C batteries, and the like. The one or more batteries may be non-rechargeable and/or non-replaceable. Preferably, the one or more batteries are disposable. Preferably, the one or more batteries are recyclable. Preferably, the one or more batteries are 9-Volt alkaline batteries. The one or more batteries are placed within the battery closure. Preferably, the one or more batteries are placed within the opposing battery support. More preferably, the one or more batteries are securely placed within a battery compartment in the opposing battery support. The batteries may be in a plurality of positions depending on the position of the battery compartment within the battery closure. Preferably, in the first position, the battery contacts are not in contact with the battery lead wires and/or terminals. Preferably, in the second position, the battery contacts are in contact with the battery lead wires and/or terminals and electricity is being transmitted from the batteries to the device. A user may prevent transmission of electricity from the battery contacts via the battery lead wires and/or terminals to the device by keeping the activation tab inserted between the battery contacts and the battery lead wires and/or terminals. A user engages the one or more batteries and the battery lead wires by moving the opposing battery support from the first position to the second position; by removing the activation tab and moving the spring-loaded members from a first position to a second position; or a combination of both moving the opposing battery support from a first position to a second position and removing the activation tab and moving the spring-loaded members from a first position to a second position. Once the opposing battery support is in the second position, the user is prevented from replacing the batteries. Once the user disables the battery lead wires, removes the opposing battery support, and the battery lead wires are severed, the removed opposing battery support contains the one or more batteries and the battery bulkhead with the severed battery lead wires; the user can then safely dispose of the batteries separately from the device.

The activation tab prevents contact of the batteries with the battery contacts, thus prolonging shelf life of the device. The activation tab can be anything performing this function. The activation tab may have any size, shape, configuration, or a combination thereof so that a user enables an electrical contact to occur between the battery lead wires and one or more battery contacts by removing the at least one activation tab. The activation tab may be made of any insulator material with high dielectric constant typically utilized in activation tabs. The activation tab may be a clear plastic. The activation tab may be a part of the battery support, the opposing battery support, or both. Preferably, the activation tab is placed between the battery contacts and the battery lead wires so that a user can pull the activation tab when the user wants to establish a contact between the battery contacts and the battery lead wires. The activation tab may be placed between the one or more terminals attached to the battery lead wires which are being biased by one or more spring-loaded members, keeping the activation tab in place before a user removes the activation tab. Preferably, the activation tab is protruding from an opening in the opposing battery support or the battery support in such a way that a user can remove the activation tab by pulling on the activation tab. For example, the activation tabs may protrude from an opening in the top part of the opposing battery support. The one or more activation tabs may protrude from between the battery support and the opposing battery support so that a user can remove the one or more activation tabs by pulling on the one or more activation tabs. The one or more activation tabs may protrude from between the battery support and the opposing battery support in the first position, the second position, or both the first position and second position. In a preferred embodiment, the housing may contain an LED activation light which illuminates upon removal of the activation tab, signaling to the user that the contact between the battery lead wires with or without terminals and the battery contacts has been established.

The mechanism disabling battery lead wires prevents supply of electrical energy from the batteries to the device; thus enforcing a single use of the device. The mechanism may be anything serving this function. The mechanism may have any size, shape, configuration, or a combination thereof. The mechanism may be made of any insulating material, such as metal, plastic, engineered ceramics, or the like. The mechanism may be located in the battery support, the opposing battery support, or both. The mechanism may contain crimped terminals soldered onto the battery lead wire, a weak solder joint between the battery bulkhead, the battery support, and the battery leads wire, a multi-strand wire with one or more pre-cut fibers, a scored or otherwise weakened portion of the battery leads wire, or the like, or a combination thereof. Preferably, the mechanism may comprise a battery bulkhead, battery bulkhead joining members, a battery bulkhead undercut, at least one arm located in the opposing battery support, a track-and-pin mechanism, a blade within the bulkhead, a barb preventing movement of the opposing battery support from the second position to the first position, or the like. In one embodiment, the mechanism may be a pin-and-track mechanism consisting of at least one arm containing at least one pin located in the opposing battery support coupled with at least one track for the at least one pin located on at least one side of the battery support. In yet another embodiment, the mechanism may be a blade located in the battery bulkhead.

The at least one arm serves as a part of a mechanism disabling battery lead wires, thus forcing a single use of the device by preventing supply of electrical energy to the device. The at least one arm can be barbed or unbarbed. The arm may be anything serving this function. The arm may have any size, shape, configuration, or a combination thereof so that (a) the arm engages into the battery bulkhead when a user puts the opposing battery support in the first position, (b) the arm locks into the undercut of the battery bulkhead in the second position, such as when a user moves the opposing battery support forward, thereby coupling the battery bulkhead to the opposing battery support, and (c) the arm lifts the battery bulkhead from the battery support when a user removes the opposing battery support from the battery closure which stresses the battery lead wires, disables the battery lead wires, and ultimately severs the battery lead wires. The at least one arm may contain at least one barb which engages the battery bulkhead preventing movement of the opposing battery support from the second position to the first position. The arm is located on the opposing battery support in such a way that the arm can engage the undercut of the battery bulkhead placed in the battery support.

The pin-and-track mechanism serves as an alternative mechanism forcing a single use of the device by disabling the battery lead wires and thus preventing supply of electrical energy to the device. The pin-and-track mechanism may be anything serving this function. The pin-and-track mechanism consists of at least one arm containing at least one pin located in the opposing battery support and at least one track for the at least one pin in the battery support. Preferably, the at least one track is located in at least one wall, such as a sidewall, of the battery support. The arm with a pin, the pin, and the track for the pin may have any size, shape, configuration, or a combination thereof so that (a) the at least one track engages the at least one pin when a user sets the opposing battery support on the battery support in the resting position, (b) the arm engages into the undercut of the battery bulkhead when the user moves the opposing battery support from the first position to the second position, such as when a user slides the opposing battery support forward, thereby coupling the battery bulkhead to the opposing battery support, (c) the arm lifts the battery bulkhead upward when the user removes the opposing battery support from the battery closure which stresses the battery lead wires, disables the battery lead wires, and ultimately severs the battery lead wires. The at least one track may contain at least one barb which engages the at least one pin preventing rearward movement of the opposing battery support from the second position to the first position.

The blade serves as another mechanism forcing a single use of the device by disabling the battery lead wires and thus preventing supply of electrical energy to device. The blade may be anything serving this function. The blade can be made of any material typically utilized in blades severing wires such as a metal, engineered ceramic, or the like. The blade may have any size, shape, configuration, or a combination thereof so that when a user removes the opposing battery support from the battery closure, the blade disables and severs the battery lead wires. Preferably, the blade is placed in the battery bulkhead. Preferably, the battery lead wires run above one or more exposed areas of the blade. More preferably, the blade has two exposed areas which disable and sever the battery lead wires running above the two exposed areas when a user removes the opposing battery support together with the bulkhead which pulls the blade upward across the battery wire leads.

The housing holds, secures, and protects working components used to operate the device. The housing can be any structure that performs this function. The housing may have any size, shape, configuration, or a combination thereof so that the housing can be gripped with a left hand, right hand, or both. Preferably, the housing has an ergonomic shape. The housing may be made of any material commonly utilized in housings of devices, such as plastic, metal, or the like. Preferably, the housing is made of a lightweight material. Preferably, the housing is made of an engineering plastic, more preferably acrylonitrile butadiene styrene (ABS), polycarbonate (PC), or a blend of ABS and PC. The housing may have an elastomer grip for better gripping and comfort. The housing may further contain a plurality of controllers, various parts of the controllers' mechanism, the like, or a combination thereof. For example, the housing may contain a shaft with different endings such as a malleable inner shaving blade, a cutter, a distal suction hole/tip; electrodes such as a monopolar electrosurgical coagulation electrode to which energy is supplied from a generator; different types of connections such as a suction connection or an irrigation connection; an LED light activation button indicating a contact has been established between the battery lead wires and the battery contacts by getting illuminated; a motor, and a motor power switch. The housing may be connected to the battery closure with an external cable. Alternatively, the housing may house the battery closure. The housing may have an additional separate cable leading to a console, for example a generator or an irrigation supply.

The motor turns electrical energy into mechanical work and powers different mechanisms of the device such as an inner blade on the device's shaft. Preferably, the motor is reliable, cost-effective, power efficient, light-weight, quiet, and has a fast dynamic response. Preferably, the motor can withstand a variety of environmental conditions to which devices used in the invention may be exposed to, for example caustic fluids, radiation, steam, varying temperatures, vacuum, and/or physical abuse. Preferably, the motor is made of a lightweight material. The motor can contain plastic, metal, and/or engineered ceramics components. The motor can be a coreless motor or have an iron-core. Preferably, the motor is a direct current (DC) motor. The DC motor can be a brushless type or a brush type motor with precious-metal brush system, carbon-brush system, or the like. The one or more batteries within the battery closure supply electrical energy to the motor.

In a preferred embodiment, the housing may contain an LED activation light indicating a contact has been established between the battery lead wires and the battery contacts and that electrical energy is being supplied to the motor of the device by getting illuminated. The LED activation light can be anything that performs this function. The LED activation light may have any size, material, shape, type, configuration, or a combination thereof. The LED activation light can be placed anywhere within or on the housing. Preferably, the LED activation light is placed on the housing in such a way that a user can see the LED activation light while holding and operating the device and is alerted when the light illuminates.

The housing may be connected to the battery closure with an external cable. The external cable transmits electrical power from the battery closure to the housing. The cable may have any size, material, shape, type, configuration, or a combination thereof. Preferably, the power cable has sufficient length to connect the battery closure to the housing while giving a user the option to keep the battery closure away from the workplace such as to keep a sterile environment around a patient. The cable may use copper, aluminum, or solid conductors. The cable is insulated. Preferably, the cable is flexible so that it can be wound and repeatedly moved. Preferably, the cable is wired to the battery closure. The cable may contain attachments such as a suction hose clip which allows for suction tubing to be kept safely out of the user's way. The cable may contain motor lead wires and/or radiofrequency lead wires. The cable may have an extension leading from the battery closure to a console such as a generator or an irrigation device. The cable may contain a plug for interfacing the generator such as a universal monopolar plug.

To operate the invention, a user can assemble the destructive battery closure by inserting one or more batteries into an opposing battery support and subsequently placing the opposing battery support in the first and second positions into the battery support. Alternatively, the batteries may be inserted into the battery support. A user can ensure a proper closure by activating a mechanism for ensuring a secure fit of the opposing battery support into the battery support, such as snapping, clicking, latching, sliding, or the like, opposing battery support into the battery support. Alternatively, a user may receive an already assembled destructive battery closure batteries secured within the opposing battery support in the first or second position. Once assembled, a user may enable transmission of electricity from the batteries to the device by setting the device into the second position. The second position may include moving the opposing battery support from a first position to a second position, such as by sliding the opposing battery support forward; moving the spring-loaded members from a first position to a second position, such as by removing the activation tab; or a combination of both moving the opposing battery support from a first position to a second position and moving the spring-loaded members from a first position to a second position. A user may check whether the contact between the battery lead wires and the battery contacts has been establish by seeing an LED activation indicator on the housing of the device light up. Alternatively, a user may follow signage on the battery support, the opposing battery support, or both to visually see a confirmation that the battery closure is in the first position or the second position. Once the user establishes the contact between the battery lead wires and the battery contacts, the user enables transmission of electric current from the batteries to the device's functioning portions which the user may then use. While assembling the battery closure and/or establishing contact between batteries and the device, a user may activate a plurality of parts of a mechanism for disabling battery lead wires. A user may couple the battery bulkhead with or without the blade to the battery support by the first bulkhead joining member when the user sets the opposing battery support in the first position. A user may release the battery bulkhead with or without the blade from the first battery bulkhead joining member and couple the battery bulkhead into the opposing battery support by moving the opposing battery support into the second position. A user may engage at least one arm of the opposing battery support into the battery bulkhead in the first position. Alternatively, a user may engage a pin of the opposing battery support into the track of the battery support in the second position. A user may prevent movement of the opposing battery support from the second position to the first position by engaging the at least one barb on the at least one arm to the battery bulkhead. Alternatively, a user may prevent movement of the opposing battery support from the second position to the first position by engaging the at least one barb on the at least one track to the at least one pin on the opposing battery support. After the user no longer uses the device, the user may disable the battery lead wires. A user may disable the battery lead wires by removing the opposing battery support with coupled battery bulkhead from the battery closure which stretches the battery lead wires. A user may remove the opposing battery support by prying, lifting, pulling, forcing, cutting, unsnapping, unhooking, releasing, disattaching, sliding, or the like the opposing battery support or the front portion of the opposing battery support from the battery support. A user may disassemble the battery closure by removing the opposing battery support with the coupled battery bulkhead from the battery closure which severs the battery lead wires. A user may dispose of the opposing battery support with the coupled battery bulkhead and batteries separately from the device. A user may recycle the batteries.

FIG. 1 illustrates one example of an article including a battery closure (1) of the teachings herein. As illustrated, a disposable medical device, a debrider (50) comprises a housing (52) including a motor (51) (not depicted), a rotating nose cone (56), an external tube with a blade (57), a suction port (58), and an LED activation light (53). A battery closure (1) comprising an opposing battery support (3) and a battery support (2) is attached to the device (50) with an external cable (54). A plug (55) is attached to a cable running from the battery closure (1) to an external functional system. The battery closure (1) supplies electrical energy to the motor (51) (not depicted) of the device (50).

Figure 2:
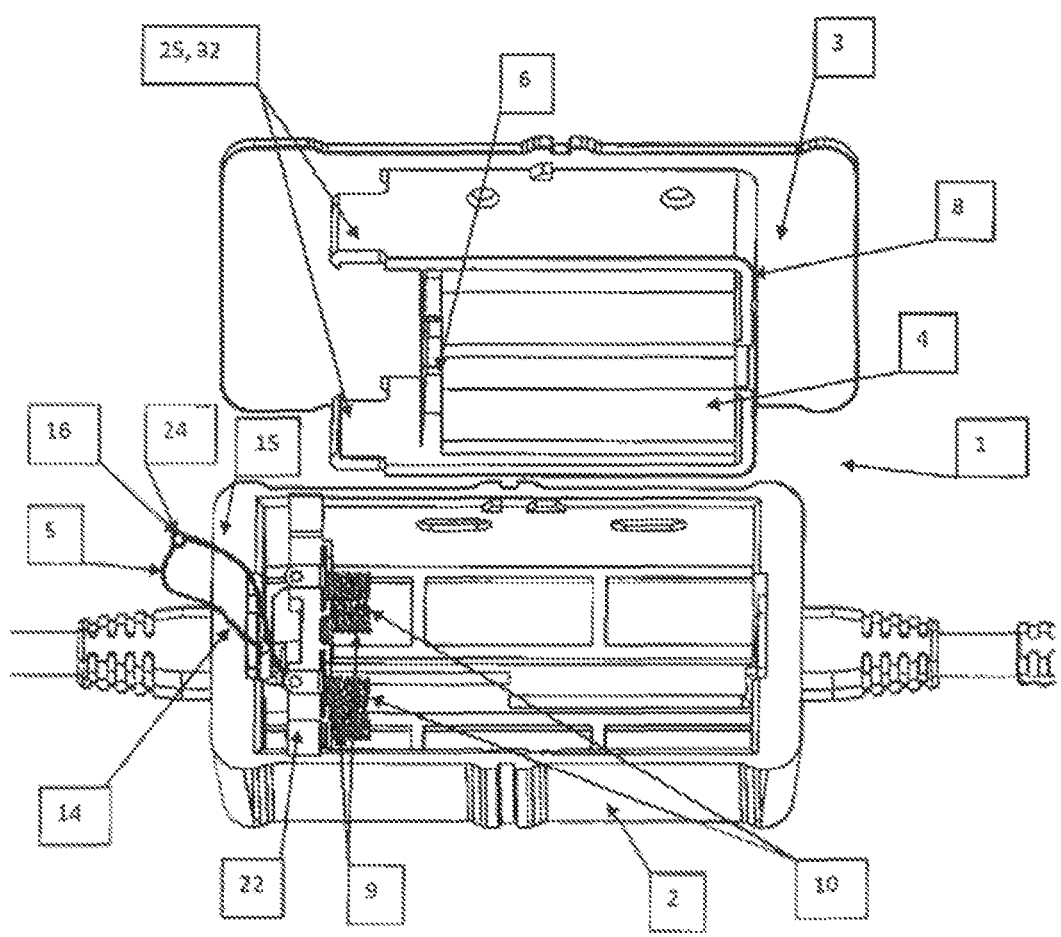
FIG. 2 illustrates a battery support and an opposing battery support before the battery closure is assembled.

FIG. 2 illustrates a battery support (2) and an opposing battery support (3) before the battery closure (1) is assembled. As illustrated, the battery support (2) comprises a battery bulkhead (22) and the battery lead wires (5). The battery lead wires (5) contain a first section (14) attached to the battery support, a second section (15) attached to the battery bulkhead, and an intermediate section (16) containing a solder joint (24) located between the first section (14) and the second section (15). The spring-loaded members (9) are attached to the battery bulkhead (22) and to the terminals (10). The opposing battery support (3) comprises a battery compartment (8) housing batteries (4) including battery contacts (6) and two arms (25) which serve a second battery bulkhead joining member (32), attaching the battery bulkhead (22) to the opposing battery support (3) when a user moves the opposing battery support (3) to the second position.

Figure 3:
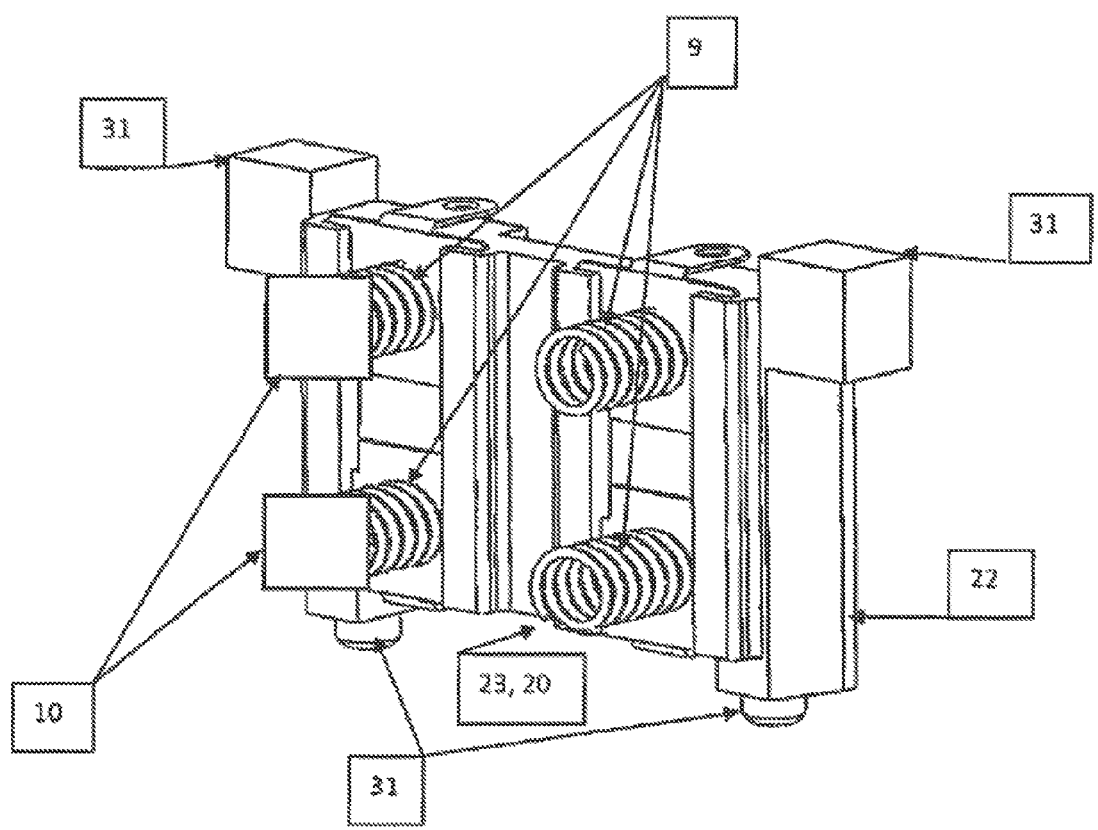
FIG. 3 illustrates a battery bulkhead of the battery support of FIG. 2.

FIG. 3 illustrates a battery bulkhead (22) of the battery support (2) (not depicted) of FIG. 2. The battery bulkhead (22) has an undercut (23) which serves as a part of a mechanism for disabling battery lead wires (20). As illustrated, spring-loaded members (9) are attached to the battery bulkhead (22) and to the terminals (10). The battery bulkhead further comprises first battery bulkhead joining members (31) attaching the battery bulkhead (22) to the battery support (2) (not depicted) when the opposing battery support (3) (not depicted) is in the first position.

Figure 4:
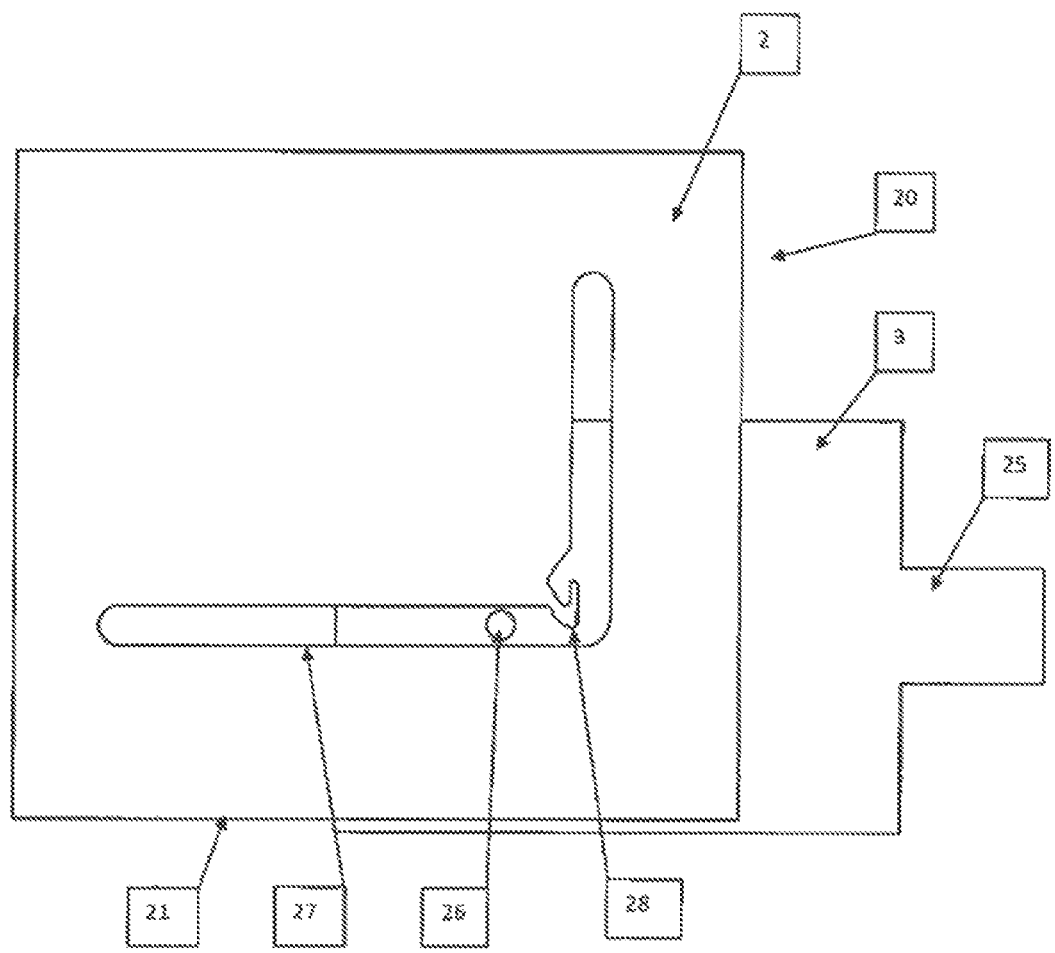
FIG. 4 illustrates a mechanism for disabling battery lead wires.

FIG. 4 illustrates a mechanism for disabling battery lead wires (20). As illustrated, the mechanism (20) comprises an arm (25) with one pin (26) on the opposing battery support (3). The mechanism (20) further comprises a track (27) on a sidewall (21) of the battery support (2) to engage the pin (26). The track (27) further contains a barb (28) preventing rearward movement of the pin (26) when the opposing battery support (3) is in the second position.

Figure 5A:
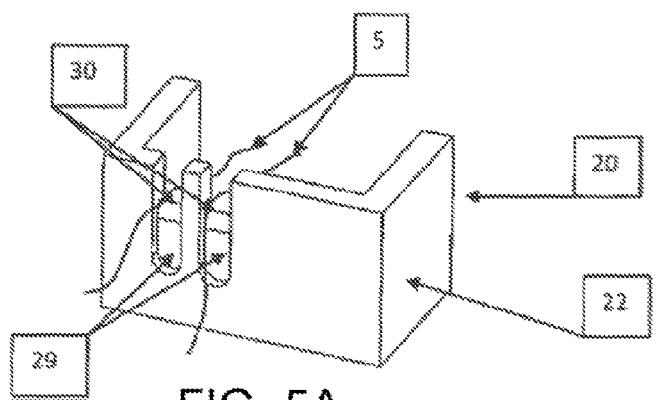
FIG. 5A illustrates a mechanism for disabling battery lead wires.

FIG. 5A illustrates an alternative mechanism for disabling battery lead wires (20). As illustrated, the battery bulkhead (22) contains a blade (29). The blade (29) has two exposed portions (30) the battery lead wires (5) run above. The blade (29) severs the battery lead wires (5) when a user removes the battery cover (3) (not depicted) with the coupled battery bulkhead (22) from the assembled battery closure (1) (not depicted) which pulls the blade (29) upward across the battery lead wires (5).

Figure 5B:
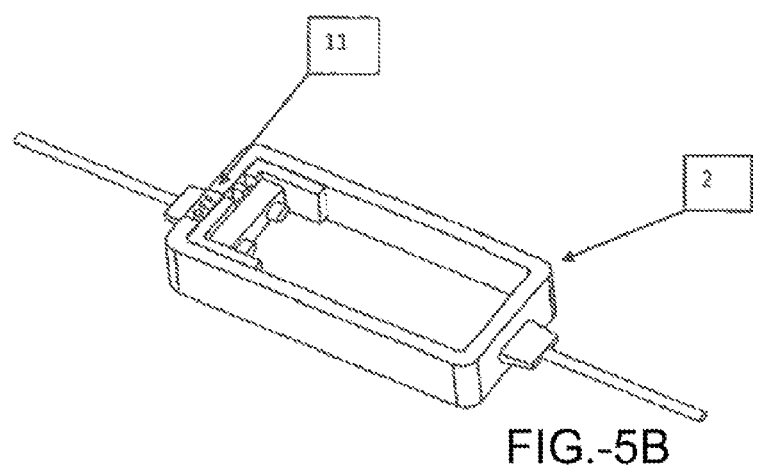
FIGS. 5B and 5C illustrate the battery support and the opposing battery support containing signage for user's visual guidance concerning the position of the opposing battery support.
Figure 5C:
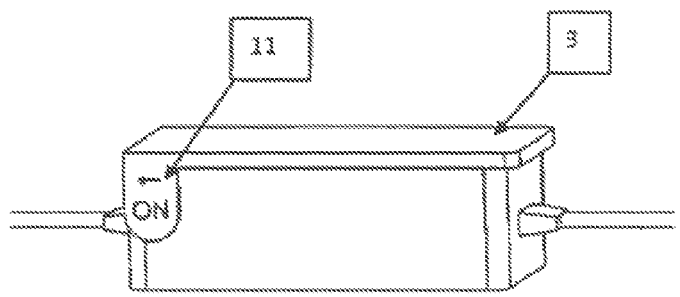

FIGS. 5B and 5C illustrate the battery support (2) and the opposing battery support (3) containing signage (11) for user's visual guidance concerning the position of the opposing battery support (3).

Figure 6:
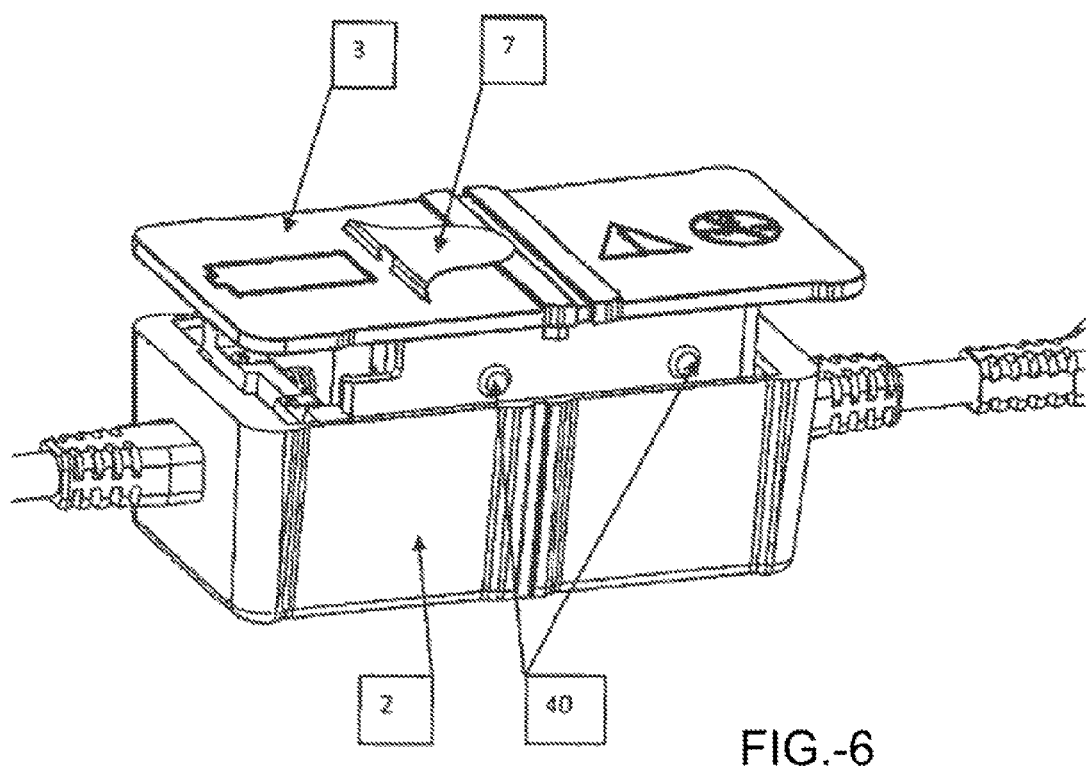
FIG. 6 illustrates an opposing battery support of FIG. 2 positioned on the battery support in the resting position.

FIG. 6 illustrates an opposing battery support (3) of FIG. 2 positioned on the battery support (2) in the resting position. The opposing battery support (3) comprises an activation tab (7) which once removed, enables contact between the battery lead wires (5)(not depicted) and battery contacts (6)(not depicted). The opposing battery support (3) further contains two prongs which are part of a mechanism for ensuring a secure fit (40) of the opposing battery support (3) into the battery support (2).

Figure 7:
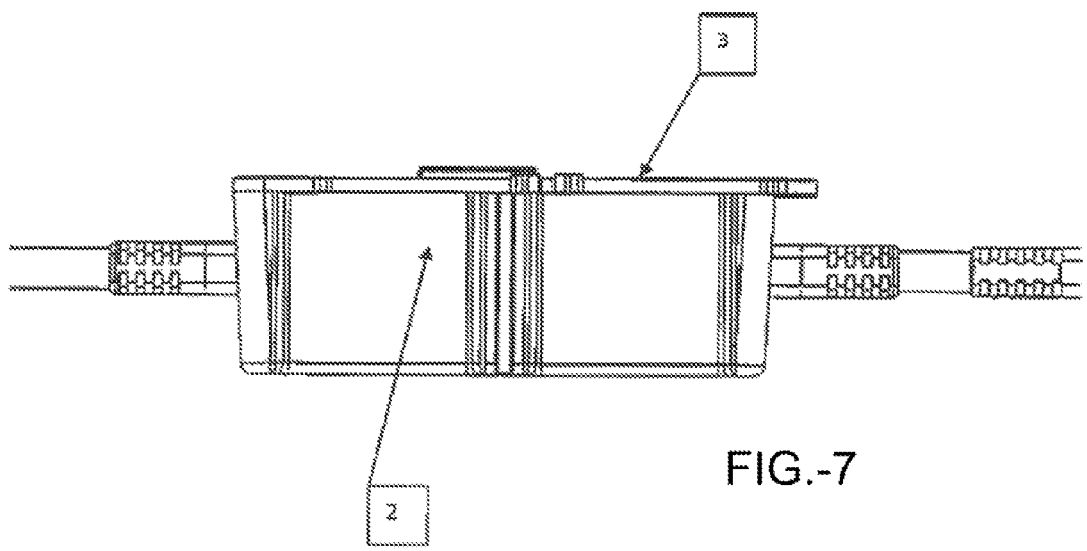
FIG. 7 illustrates the opposing battery support of FIG. 2 positioned in the first position.

FIG. 7 illustrates the opposing battery support (3) of FIG. 2 positioned in the first position. As illustrated, the opposing battery support (3) is completely inserted into the battery support (2). The opposing battery support's (3) front edge is flush with the front edge of the battery support (2).

Figure 8:
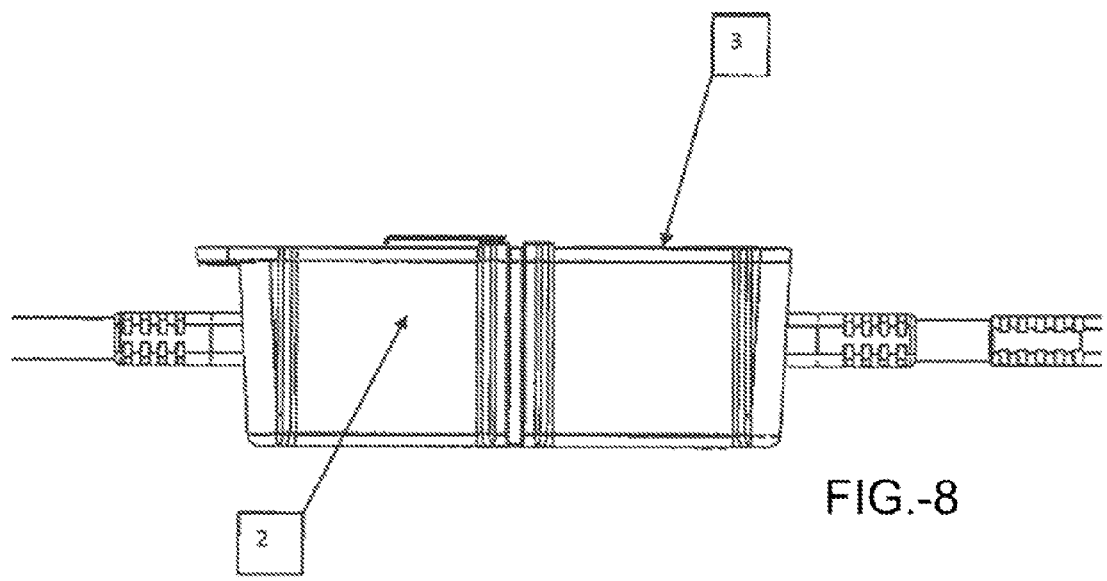
FIG. 8 illustrates the opposing battery support of FIG. 2 slid forward to the second position.

FIG. 8 illustrates the opposing battery support (3) of FIG. 2 moved forward to the second position. As illustrated, the opposing battery support's (3) front edge extends over the front edge of the battery support (2).

Figure 9:
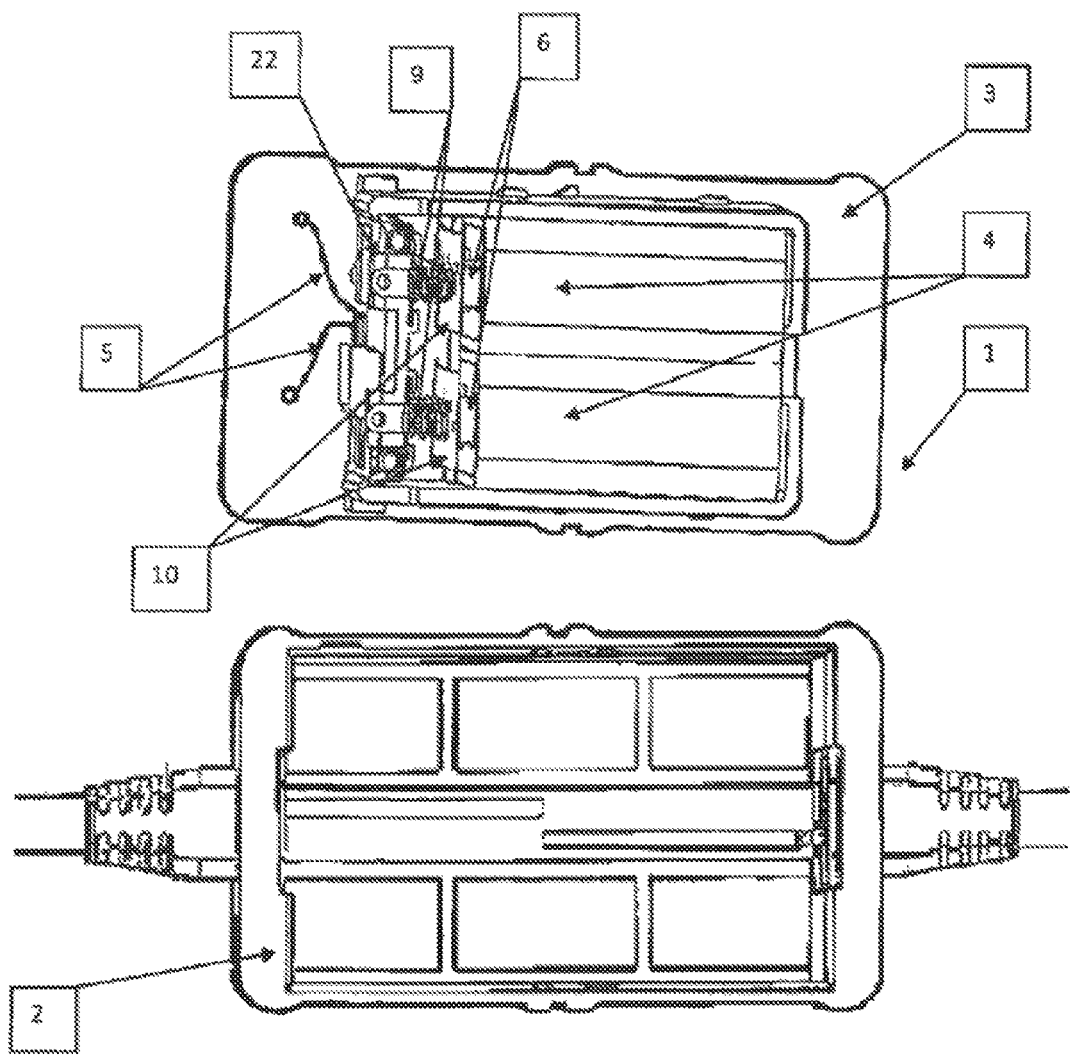
FIG. 9 illustrates the disassembled battery closure of FIG. 1 after the opposing battery support has been removed from the battery closure.

FIG. 9 illustrates the disassembled battery closure (1) of FIG. 1 after the opposing battery support (3) with the coupled battery bulkhead (22) has been removed from the battery support (2). The opposing battery support (3) contains the batteries (4) with the battery contacts (6) and the coupled battery bulkhead (22) with the severed battery lead wires (5). The spring-loaded members (9) are attached to the battery bulkhead (22) and the terminals (10). The battery support (2) is ready for disposal with the device (50) (not depicted) as medical waste separate from the opposing battery support (3) with attached batteries (4).

Figure 10:
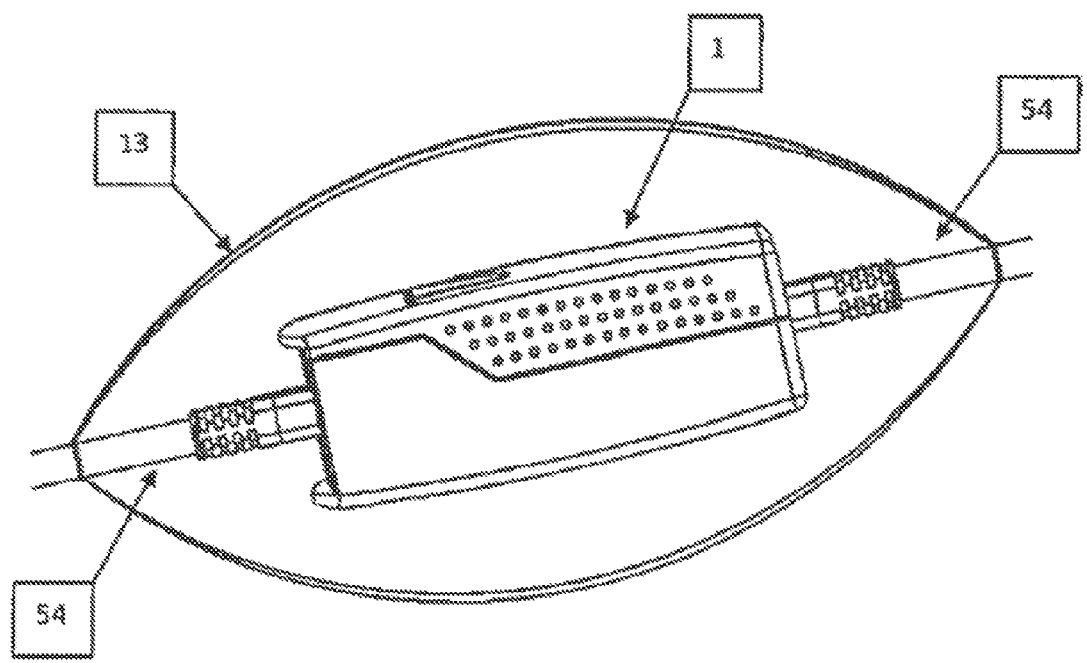
FIG. 10 illustrates the battery closure having an elastic member over the battery closure to protect the battery closure against a variety of environmental conditions.

FIG. 10 illustrates the battery closure (1) having an elastic member (13) over the battery closure (1) to protect the battery closure (1) against a variety of environmental conditions the device (50) (not depicted) may be exposed to. The elastic member (13) is attached to the external cable (54).

Figure 11:
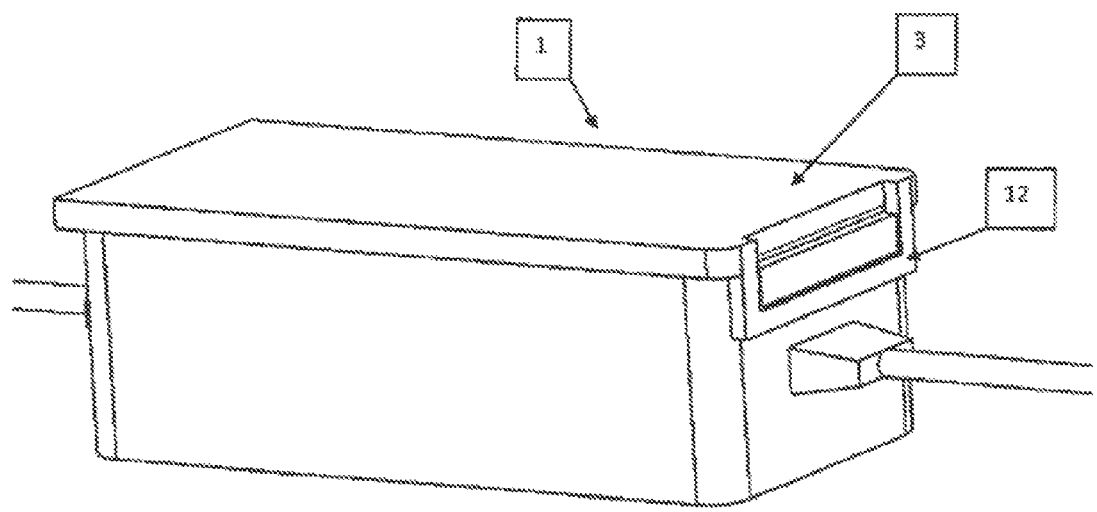
FIG. 11 illustrates the battery closure with the opposing battery support in the engaged position having a rear lock.

FIG. 11 illustrates an alternative embodiment of the battery closure (1) with the opposing battery support (3) in the engaged position having a lock (12) at the rear side.

Figure 12:
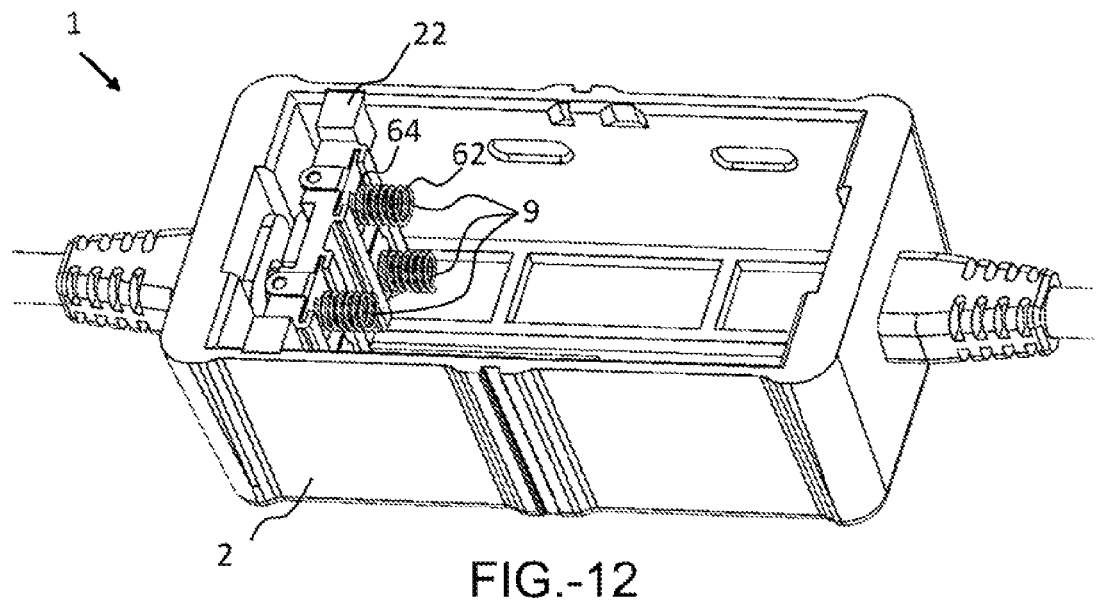
FIG. 12 illustrates a battery bulkhead member within the battery support.

FIG. 12 illustrates the battery support (3) of the battery closure (1) with the opposing battery support (3) (not shown) removed. The battery support (3) comprises a battery bulkhead (22). Connected to the battery bulkhead (22) are one or more spring-loaded members (9). Each spring-loaded member (9) comprises a first end (62) and a second end (64). The spring-loaded members (9) are connected to the battery bulkhead (22) at the second end (64). The spring-loaded members (9) may be attached to one or more terminals (10) (not shown) at the first end (62). The one or more spring-loaded members (9) may drive the one or more terminals (10) into contact with an activation tab (7) (not shown).

Figure 13:
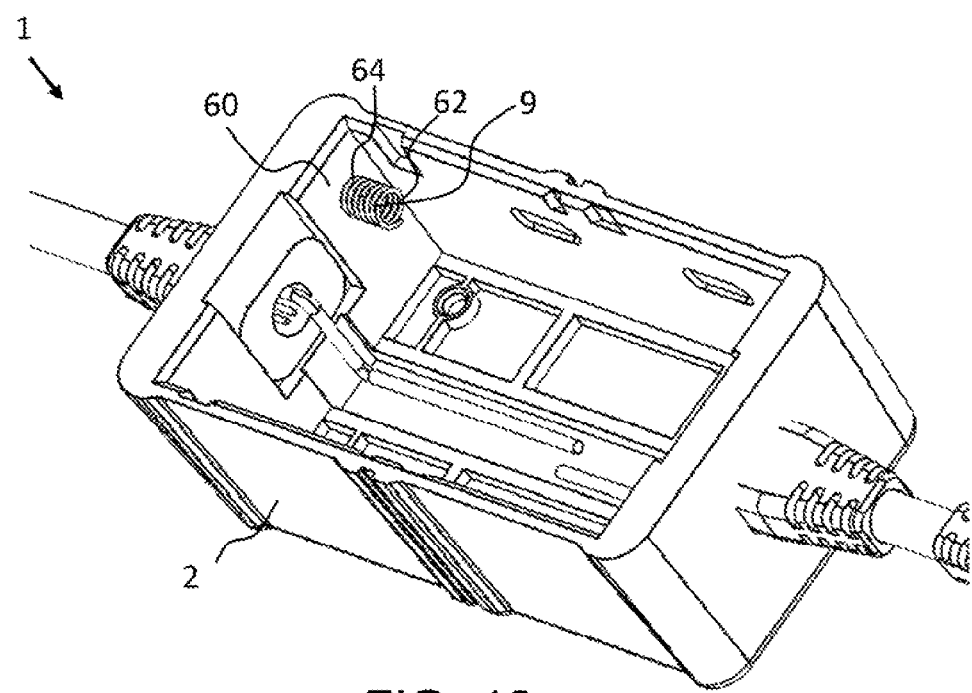
FIG. 13 illustrates a spring-loaded member attached to the battery support.

FIG. 13 illustrates the battery support (3) of the battery closure (1) with the opposing battery support (3) (not shown) removed. The battery support (3) comprises an inner-wall (60). The inner wall (60) is an anchoring surface for one or more spring-loaded members (9). The spring-loaded members comprise a first end (62) and a second end (64). The spring-loaded members (9) are connected to inner wall (60) at the second end (62). The spring-loaded members (9) may be attached to one or more terminals (10) (not shown) at the first end (62). The one or more spring-loaded members (9) may drive the one or more terminals (10) into contact with an activation tab (7) (not shown).

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. An article comprising:
   (a) a battery support containing battery lead wires attached to one or more terminals;
   (b) an opposing battery support attached to the battery support to create a battery closure;
   (c) one or more batteries having one or more battery contacts in the opposing battery support;
   (d) one or more activation tabs; and
   (e) one or more spring-loaded member shaving a linear axis;
      wherein the one or more terminals are attached to the one or more spring-loaded members;
      wherein the one or more activation tabs are spaced between the one or more terminals and the one or more battery contacts;
      wherein the one or more spring-loaded members provide a biasing force that biases the one or more terminals against the one or more activation tabs keeping the one or more activation tabs in place in either a first position or a second position of the opposing battery support;
      wherein the opposing battery support is moveable from the first position to the second position relative to the battery support by moving the opposing battery support along the linear axis and toward the one or more spring-loaded members to compress the one or more spring-loaded members so that the biasing force is greater in the second position than in the first position; and
      wherein the opposing battery support is securely connected to the battery support in both the first position and the second position.

2. The article of claim 1, wherein the one or more spring-loaded members are one or more compression springs having a first end connected to the one or more terminals.

3. The article of claim 1, wherein the one or more spring-loaded members hold the one or more activation tabs between the one or more terminals and the one or more battery contacts, before the one or more activation tabs are removed from the article.

4. The article of claim 3, wherein the one or more activation tabs prevent contact between the one or more battery contacts and the one or more terminals in both the first position and the second position.

5. The article of claim 4, wherein the one or more spring-loaded members drive the one or more terminals into contact with the one or more battery contacts once the one or more activation tabs are removed.

6. The article of claim 5, wherein contact between the one or more terminals and the one or more battery contacts engages the one or more batteries and enables transmission of electrical energy from the one or more batteries to the battery lead wires.

7. The article of claim 1, wherein the one or more spring-loaded members are placed between the one or more terminals and an anchoring surface.

8. The article of claim 7, wherein the one or more spring-loaded members are one or more compression springs having:
   a) a first end connected to the one or more terminals; and
   b) a second end connected to the anchoring surface.

9. The article of claim 8, wherein a distance between the one or more terminals and the anchoring surface is greater in the first position than in the second position.

10. The article of claim 9, wherein the article comprises a battery bulkhead attached to both the battery support and the opposing battery support; and the anchoring surface is part of the battery bulkhead.

11. The article of claim 9, wherein the anchoring surface is part of the battery support.

12. The article of claim 11, wherein the anchoring surface is an interior wall of the battery support.

13. The article of claim 1, wherein the article comprises a battery bulkhead attached to both the battery support and the opposing battery support; and
   wherein the one or more spring-loaded members are placed between the battery bulkhead and the one or more terminals.

14. The article of claim 13, wherein the one or more spring-loaded members are one or more compression springs having:
   a) a first end connected to the one or more terminals; and
   b) a second end connected to the battery bulkhead;
   wherein a distance between the one or more terminals and the battery bulkhead is greater in the first position than in the second position.

15. The article of claim 1, wherein the one or more spring-loaded members are placed between an anchoring surface of the battery support and the one or more terminals; and
   wherein the anchoring surface is an interior wall of the battery support.

16. The article of claim 1, wherein either the battery support or the opposing battery support has an opening; and
   wherein the one or more activation tabs protrude from the opening so that a user can remove the one or more activation tabs by pulling on the one or more activation tabs.

17. The article of claim 1, wherein the one or more activation tabs protrude from between the battery support and the opposing battery support so that a user can remove the one or more activation tabs by pulling on the one or more activation tabs.

18. A method comprising the following steps:
   (i) preventing supplying energy to a device by:
   (a) assembling a battery closure by connecting a battery support to an opposing battery support, wherein the battery support contains battery lead wires attached to one or more terminals, one or more batteries are secured to the opposing battery support, and the one or more batteries have one or more battery contacts;
   (b) preventing engaging the one or more batteries by one or more spring-loaded members which provide a biasing force that biases the one or more terminals against one or more activation tabs when the opposing battery support is in either a first position or a second position, wherein the one or more activation tabs are spaced between the one or more terminals and the one or more battery contacts;
   (ii) supplying energy to the device by:
   (a) removing the one or more activation tabs;
   (b) driving the one or more terminals by the one or more spring-loaded members into contact with the one or more battery contacts so as to engage the one or more batteries and the battery lead wires to establish contact between the one or more battery contacts and the battery lead wires; and
   wherein the one or more spring-loaded members have a linear axis;
   wherein the opposing battery support is moveable from the first position to the second position relative to the battery support by moving the opposing battery support along the linear axis and toward the one or more spring-loaded members to compress the one or more spring-loaded members so that the biasing force is greater in the second position than in the first position, and
   wherein the opposing battery support is securely connected to the battery support in both the first position and the second position.

19. The method of claim 18, wherein the step of supplying energy to the device can occur in either the first position or the second position.

20. The method of claim 18, comprising a step of disabling supplying energy to the device by removing the opposing battery support from the battery closure to disable transmission of electricity.

* * * * *

UNITED STATES PATENT AND TRADEMARK OFFICE
CERTIFICATE OF CORRECTION

PATENT NO. : 9,692,036 B2
APPLICATION NO. : 14/703158
DATED : June 27, 2017
INVENTOR(S) : Michael J. Bennett et al.

It is certified that error appears in the above-identified patent and that said Letters Patent is hereby corrected as shown below:

Column 18, Line 14 delete "member shaving" and insert --members having--

Signed and Sealed this
Seventh Day of November, 2017

Joseph Matal
*Performing the Functions and Duties of the*
*Under Secretary of Commerce for Intellectual Property and*
*Director of the United States Patent and Trademark Office*